US012178934B2

United States Patent
Ford et al.

(10) Patent No.: US 12,178,934 B2
(45) Date of Patent: Dec. 31, 2024

(54) MEDICAL INSTRUMENT STERILIZATION BACKER CARD

(71) Applicant: SterileBits, Inc., Kemah, TX (US)

(72) Inventors: Craig Ford, Marina del Rey, CA (US); Guy Brent Phipps, Long Beach, CA (US); William Lawrence Patton, III, Rancho Mirage, CA (US); Robert James Jones, Cedar Park, TX (US)

(73) Assignee: SterileBits, Inc., Kemah, TX (US)

( * ) Notice: Subject to any disclaimer, the term of this patent is extended or adjusted under 35 U.S.C. 154(b) by 107 days.

(21) Appl. No.: 18/099,675

(22) Filed: Jan. 20, 2023

(65) Prior Publication Data

US 2023/0149584 A1     May 18, 2023

Related U.S. Application Data

(63) Continuation-in-part of application No. 17/160,816, filed on Jan. 28, 2021, now Pat. No. 11,717,371.

(60) Provisional application No. 63/304,901, filed on Jan. 31, 2022.

(51) Int. Cl.
    *A61L 2/28*     (2006.01)
    *A61L 2/07*     (2006.01)
    *A61L 2/20*     (2006.01)

(52) U.S. Cl.
    CPC ...... *A61L 2/28* (2013.01); *A61L 2/07* (2013.01); *A61L 2/206* (2013.01); *A61L 2202/24* (2013.01)

(58) Field of Classification Search
    CPC ... A61B 50/30; A61B 50/20; A61B 2050/314; A61B 2050/0056; A61B 2050/0065; A61B 2050/318; B65D 73/0021; B65D 73/0035; B65D 73/0042; B65D 73/0064; B65D 73/0014; B65D 73/0078; B65D 73/0085; B65D 73/00
    USPC ....... 206/495, 806, 477–479, 482, 363, 464, 206/553
    See application file for complete search history.

(56) References Cited

U.S. PATENT DOCUMENTS

| | | | |
|---|---|---|---|
| 2,118,144 | A | 8/1932 | Berman et al. |
| 3,098,751 | A | 7/1963 | Huyck et al. |
| 3,487,922 | A | 1/1970 | Peck |
| 3,604,616 | A | 9/1971 | Greif |
| 3,925,014 | A | 12/1975 | Langdon |
| 4,023,678 | A | 5/1977 | Fiedler |
| 4,043,754 | A | 8/1977 | Sklar |
| 4,142,632 | A | 3/1979 | Sandel |

(Continued)

FOREIGN PATENT DOCUMENTS

EP     0512191 A2     11/1992

OTHER PUBLICATIONS

The extended European search report for the European Application No. 23153279.7 dated Jun. 26, 2023.

*Primary Examiner* — Robert Poon
(74) *Attorney, Agent, or Firm* — KELLY & KELLEY, PLLC

(57) ABSTRACT

A medical instrument sterilization backer card includes a flap extending from an end of a base and foldable over the base to form an open-ended pocket that receives an end of a shaft of the medical instrument therein. A second flap extends from the base and is foldable over the base to form a shell defining a compartment configured to receive a head of the medical instrument therein. The assembled backer card holds and protects the medical instrument during and after sterilization.

9 Claims, 6 Drawing Sheets

(56) References Cited

U.S. PATENT DOCUMENTS

| | | | |
|---|---|---|---|
| 4,229,420 A | 10/1980 | Smith et al. | |
| 4,247,003 A | 1/1981 | Jones | |
| 4,385,692 A | 5/1983 | Eldridge, Jr. | |
| 4,506,787 A | 3/1985 | Bruso | |
| 4,597,493 A | 7/1986 | Bruso | |
| 5,351,822 A * | 10/1994 | Sinn | B65D 73/0021 |
| | | | 206/478 |
| 5,375,717 A | 12/1994 | Roshdy | |
| 5,477,964 A | 12/1995 | Hart | |
| 5,601,189 A | 2/1997 | Roshdy | |
| 5,655,657 A | 8/1997 | Roshdy | |
| 5,699,909 A | 12/1997 | Foster | |
| 5,791,470 A * | 8/1998 | Usui | B65D 73/0014 |
| | | | 206/362.4 |
| 9,439,658 B2 | 9/2016 | Ford et al. | |
| 2004/0065571 A1* | 4/2004 | Gammons | A61L 2/26 |
| | | | 206/363 |
| 2006/0016707 A1 | 1/2006 | Chow et al. | |
| 2014/0103100 A1* | 4/2014 | Falcon | B65D 73/0085 |
| | | | 229/122 |
| 2014/0343553 A1* | 11/2014 | Ford | A61B 17/1628 |
| | | | 606/80 |
| 2021/0236225 A1 | 8/2021 | Ford et al. | |

* cited by examiner

MEDICAL INSTRUMENT STERILIZATION BACKER CARD

RELATED APPLICATION

This application claims the benefit of U.S. Provisional Application No. 63/304,901filed on Jan. 31, 2022. This application is also a continuation-in-part of U.S. application Ser. No. 17/160,816, filed on Jan. 28, 2021.

FIELD OF THE INVENTION

The present invention generally relates to the sterilization of used medical instruments. More particularly, the present invention relates to a medical instrument sterilization backer card that immobilizes the medical instrument during and after the sterilization process.

BACKGROUND OF THE INVENTION

As is well known in the medical profession, the sterilization of precision medical instruments must be accomplished with certain purposes in mind. Basically, for both economic and efficiency reasons, such sterilization needs to be done in a manner which will ensure the most effective exposure of the instrument to the sterilizing medium while minimizing the possibility of contaminating the instrument prior to its use. Obviously, a major concern in this process is the actual handling of the instrument. In order to meet the need for effective handling of a medical instrument during sterilization, various packaging techniques have been proposed. The prior art devices, however, do not incorporate into one package all of the features which are deemed desirable for the most effective handling of a medical instrument during sterilization and between the time it is sterilized and its subsequent use.

One desirable feature of an instrument protector is that it immobilize the instrument. Such immobilization, particularly for medical instruments which are pointed or which have cutting or sharp edges, reduces the possibility of dulling or blunting their surfaces by contact with or rubbing against other surfaces. Yet another desirable feature for an instrument protector is the added protection it can give against an inadvertent puncturing of the outer sterilizable envelope by the instrument's sharp or pointed surfaces.

Sometimes, tip protectors are placed over the cutting ends or edges of the medical instrument. However, the tip protector's tight fit onto the instrument creates doubt as to whether the instrument gets sterilized completely. It is recommended not to use clear or colorless tip protectors in order to protect against the chance of retained surgical items in the wound by inadvertently leaving the tip protector on the medical instrument. The tip protectors are typically comprised of a plastic material, and the tip protectors and the labor required to attach and detach them may make them less convenient and more expensive than sterilization cards.

Another desirable feature is that the instrument protector present the instrument for sterilization in a configuration which will allow the greatest exposure of the instrument to the sterilizing medium. Oftentimes, the protector devices to which the medical instrument is attached prevents the sterilizing medium from freely flowing over all parts of the medical instrument to fully sterilize it.

Additionally, it is desirable if some provision is made for easy identification of the instrument. Preferably, such identification can be done visually and thus obviate the use of external labels which may cause confusion if the protector is used with a different instrument. This last consideration is particularly important when it is envisioned that any particular embodiment of a sterilizable instrument protector can be used with a plurality of different instruments.

Use of the instrument protector must be effective regardless of the particular sterilization process utilized. Two common sterilization processes include the use of steam, and in other cases ethylene oxide (ETO) which may be used when the medical instruments are moisture or heat sensitive or otherwise cannot be sterilized by steam sterilization.

Accordingly, there is a continuing need for an instrument protector which immobilizes the instrument both during and after sterilization. There is also a continuing need for an instrument protector which allows the greatest exposure of the instrument to the sterilizing medium without inadvertent puncturing. Such an instrument protector should be usable with a plurality of different instruments and allow for easy identification of the instrument. What is also needed is an instrument protector which is convenient and easy to use and relatively inexpensive. The present invention fulfills these needs and provides other related advantages.

SUMMARY OF THE INVENTION

The present invention is directed to a medical instrument protector, in the form of a medical instrument sterilization backer card, which immobilizes the medical instrument both during and after sterilization. The backer card of the present invention allows for the exposure of the medical instrument to sterilizing medium while protecting and covering points and sharp edges of the medical instrument which could otherwise inadvertently puncture an outer sterilizable envelope. The sterilization backer card of the present invention is convenient and easy to use and relatively inexpensive and allows for easy identification of the medical instrument.

The medical instrument sterilization backer card of the present invention comprises a generally planar base. A first flap extends from a first end of the base. The first flap is movable from a non-deployable position extending away from the base to a deployed position folded over the base and forming an open-ended pocket configured to receive an end of a shaft of the medical instrument therein. A second flap extends from a second end of the base. The second flap is movable between a non-deployable position extending away from the base to a deployed position over the base and forming a shell defining a compartment configured to receive a head of the medical instrument therein.

The first flap may have tabs which are insertable into tab slots formed in the base to hold the first flap in position relative to the base. The tabs may be partially inserted into the tab slots to maintain the first flap in a spaced relation to the base.

A window may be formed in the first flap. The window may facilitate visual identification of the medical instrument and/or facilitate exposure of the instrument to the sterilizing medium.

The second flap typically has multiple sections foldable relative to one another to form the shell so as to at least partially surround the head of the medical instrument. A top section of the second flap may have a window formed therein. The window may be used to facilitate exposure of the medical instrument to the sterilizing medium and/or provide easy visual identification of the medical instrument.

A locking mechanism retains the second flap into a folded, deployed position over the base. The locking mechanism may comprise a first locking member detachable from the base and a second locking member formed in the second flap that lockingly engages the first locking member. The first locking member may comprise a belt partially detachable from the base, and the second locking member may comprise a slit formed in the second flap. The belt extends over the deployed second flap and into the slit. The first locking member may instead comprise a wall lifted upwardly from the base and having a slot formed therein. A wing formed in the second flap is insertable into the slot wall and forms the second locking member.

A sterilization indicator retainer may be formed in the base for holding a sterilization indicator or integrator therein.

A fingerhold may extend from the base which has an aperture sized for insertion of a finger therethrough for lifting and moving the sterilization backer card and attached medical instrument. Alternatively, or in addition, a fingerhold aperture may be formed through the base which is sized for insertion of a finger therethrough.

An eyelet may be formed in the base intermediate the ends thereof which has an aperture or notch formed therein. The eyelet is pivotable upwardly from the base to receive the shaft of the medical instrument. Alternatively, or additionally, a notch may be formed in the second flap that receives the shaft of the medical instrument therein.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 3 is a top view of the backer card of FIG. 2 supporting a medical instrument, in accordance with the present invention;

DETAILED DESCRIPTION OF THE PREFERRED EMBODIMENTS

Figure 1:
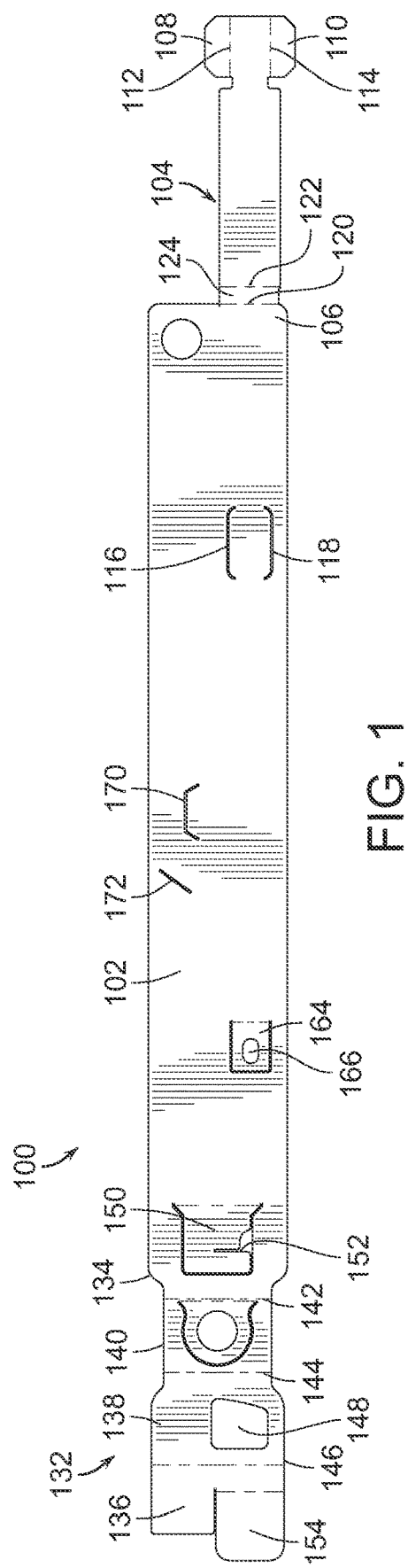
FIG. 1 is a top view of a medical instrument sterilization backer card in an unfolded state.

As shown in the accompanying drawings and photographs, for purposes of illustration, the present invention is directed to an instrument protector backer card, generally referred to by the reference number 100, for holding and protecting a medical instrument. The instrument protector backer card 100 provides a mounting surface configured to hold and maintain and protect a medical instrument, such as for sterilization and the like.

The backer card 100 is comprised of a material which can be printed and/or dye cut, subjected to sterilizing steam and/or chemicals, and which can securely and protectively hold a medical instrument 10, typically a medical or surgical instrument or the like, thereon such as for sterilization processes and the like. The backer card 100 of the present invention is typically comprised of a paper material of a sufficient thickness, such as at least 14 pt. thickness, so as to securely hold the instrument 10 thereon and enable certain aspects of the backer card 100 to be manually bent, folded and the like by the user when attaching the medical instrument 10 thereto. In a particularly preferred embodiment, the backer card 100 is comprised of a solid bleached sulfate (SBS), which is a bleached virgin fiber grade of paper board of high quality. It has been found that using a 14 pt. paper board material enables the user to manually manipulate and articulate portions of the backer card 100 while retaining the medical instrument 10 securely on the backer card. The SBS paper board material is steam sterilization and ethylene oxide friendly.

While the medical instrument protector backer card 100 of the present invention could be used with a variety of devices, and is particularly configured for use with medical instruments having a head 12 and shaft 14 portions. In a particularly preferred embodiment, the instrument protector backer card 100 is configured for use with a Davinci instrument having a head portion 12 and a shaft 14 extending therefrom, such as used in Davinci robotic surgical systems. The end of the shaft or jaw 16 of such systems may have attached thereto various accessories, such as hooks, forceps, drivers, etc., needed for surgical purposes. The entire medical instrument 10, including the head 12, shaft or jaw 14, and attached accessory can be supported and protected when partially enveloped and held in place on the folded instrument protector backer card 100 of the present invention. This enables the medical device 10 to be sterilized, stored, transported, etc. when connected to and supported by the instrument protector backer card 100 of the present invention.

With reference now to FIG. 1, a backer card 100 embodying the present invention is shown in an unfolded state. The backer card 100 has a generally planar base 102 forming an elongated middle portion of the unfolded backer card 100, as illustrated in FIG. 1. The base 102 serves as a support member for the medical device 10.

Figure 2:
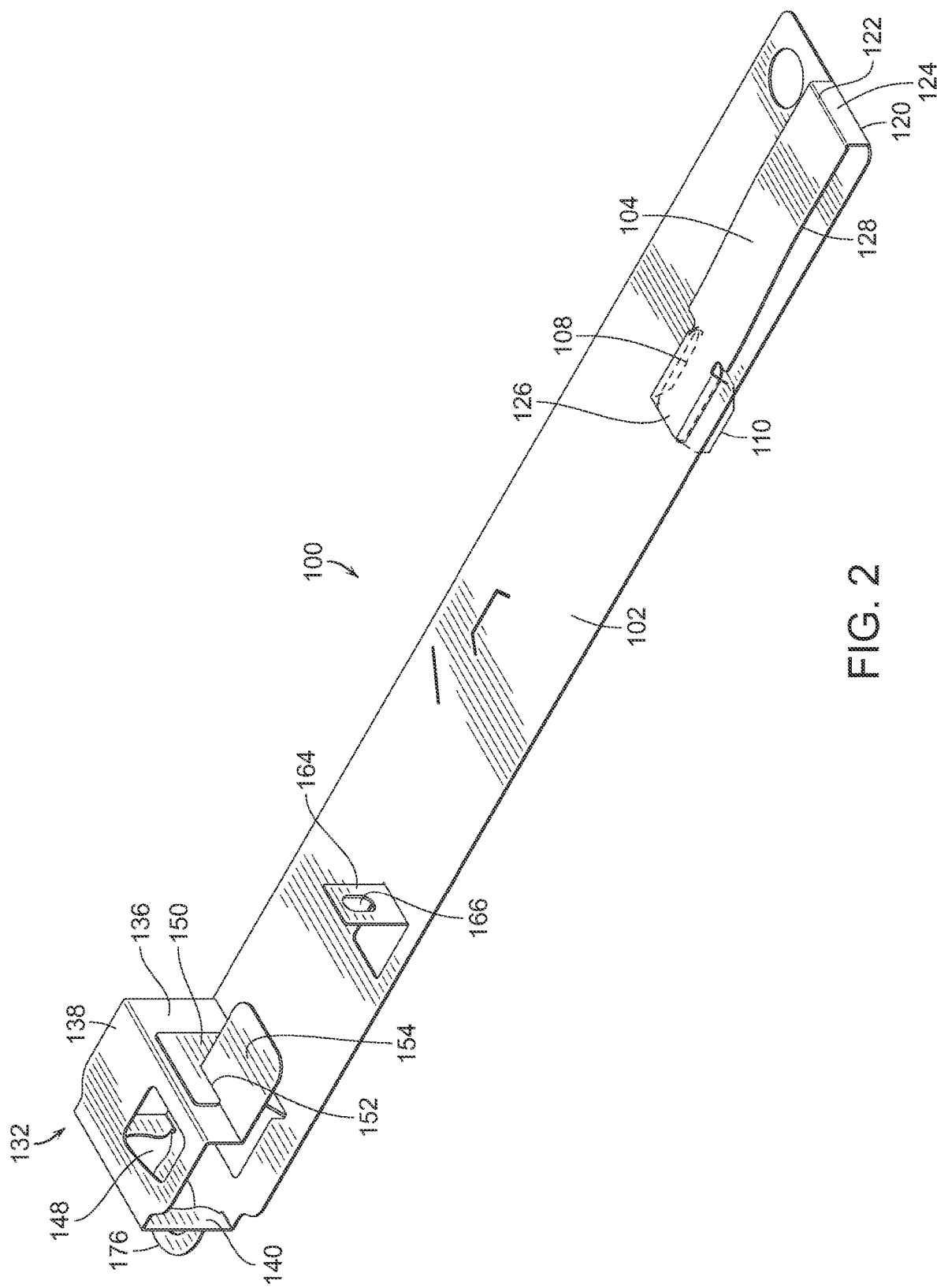
FIG. 2 is a side perspective view of the backer card of FIG. 1 in a folded state.

A first flap 104 extends from a first end 106 of the base 102. The first flap 104 is movable from a non-deployed position, extending away from the base 102, as illustrated in FIG. 1, to a deployed position folded over the base 102 to form an open-ended pocket which receives an end 16 of the shaft 14 of the medical instrument 10 therein, as illustrated in FIGS. 2 and 3. As illustrated in FIGS. 1-3, the flap 104 is elongated, such as being preferably of a sufficient length so that an end portion 16 of shaft 14 of different lengths or configurations may be inserted therein to accommodate different medical instruments or medical instruments having varying shaft lengths. The flap 104, as illustrated in FIGS. 1-3, is of a width less than that of the base 102, such as being approximately one-half or less the width of the base 102, although it is not necessarily limited to such.

The first flap 104 may include tabs 108 and 110 which may be folded from a generally planar position, as illustrated in FIG. 1, to a downward position, as illustrated in FIGS. 2 and 3. Score lines 112 and 114 may be used to assist in the folding of the tabs 108 and 110. The tabs 108 and 110 are insertable into tab slots 116 and 118 formed in the base 102 a distance from end 106 corresponding to the length of the flap 104. The tabs 108 and 110 may be of a height or dimension so as to extend upwardly from the base 102 after being inserted, or partially inserted, in tab slots 116 and 118 such that the first flap 104 is spaced from the base 102 a desired distance.

With reference now to FIGS. 1 and 2, the first flap 104 extends from the first end 106 of the base 102 along a score line or fold line 120. This facilitates the folding of the flap 104 over the base 102 when moved from a non-deployed position to a deployed position, as mentioned above. A second score line or fold line 122 may be formed a distance from the first score line 120 to form a wall 124 comprised of the space between the score lines 120 and 122. This wall, as illustrated in FIG. 2, also raises the flap 104 a distance from the base 102 to provide a compartment of a desired dimension within the pocket cooperatively formed by the deployed flap 104 and base 102. The space between the flap 104 and the base 102 can be altered by altering the distance between fold or score lines 120 and 122. Such spacing can also, or alternatively, be altered by increasing or decreasing the size of tabs 108 and 110. As illustrated, the use of the tabs 108 and 110 and the wall 124 formed by the space between score lines 120 and 122 cooperatively raise the flap 104 a distance from the base 102 to create a compartment within the pocket in which the end 16 of the shaft 14 of the medical instrument 10 can reside. Such a compartment within the pocket may enable the end 16 of the shaft to not come into contact with the base 102, flap 104, or other structure of the backer card 100 when the end 16 of the shaft 14 is inserted into the pocket.

The pocket formed by the base 102 and flap 104 has an opening 126 for insertion of the shaft 10 therethrough. In a particularly preferred embodiment, as illustrated, the pocket is open-ended, with the opening 126 being defined by substantially the length or width of the end of the flap 104. In this manner, ends of medical instruments having varying sizes or configurations may be inserted into the pocket 128.

Figure 5:
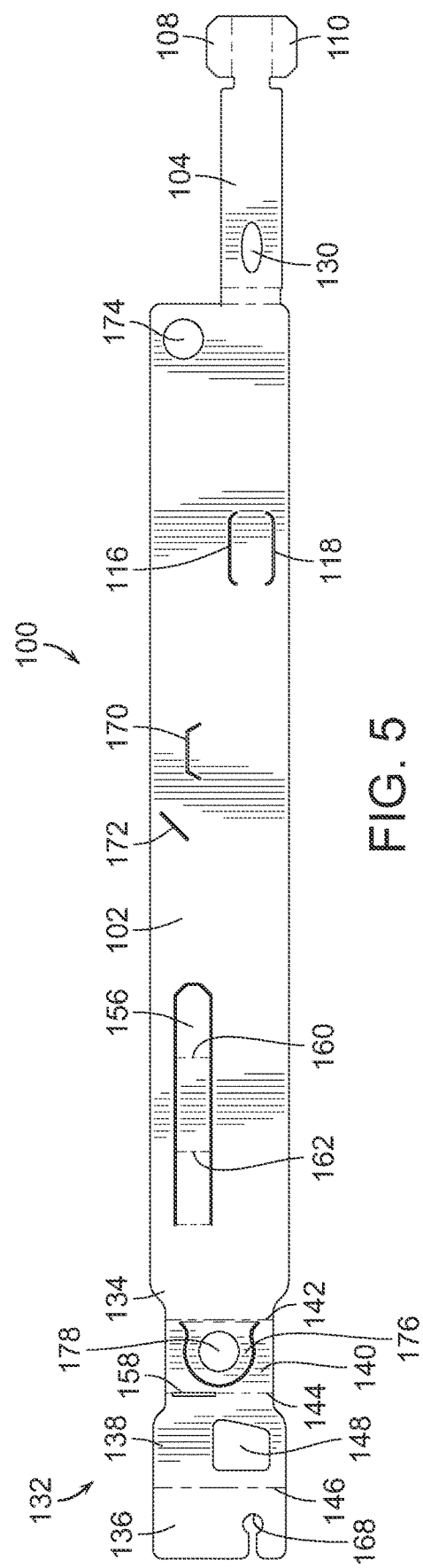
FIG. 5 is a top view of a medical instrument sterilization backer card embodying the present invention.
Figure 7:
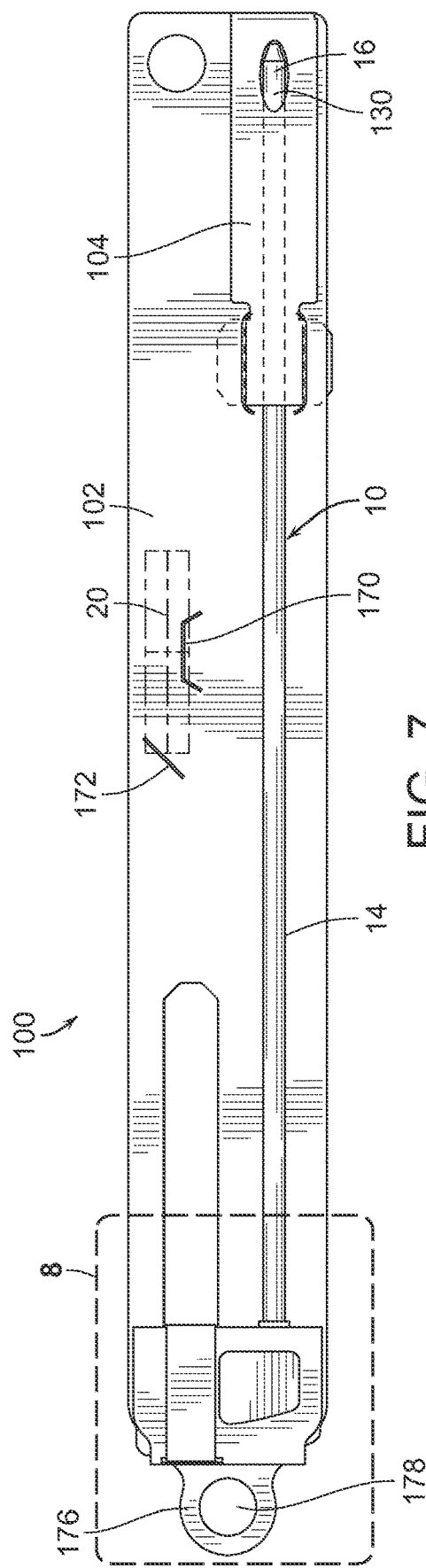
FIG. 7 is a top plan view of the backer card of FIG. 6, supporting a medical instrument thereon, in accordance with the present invention.
Figure 6:
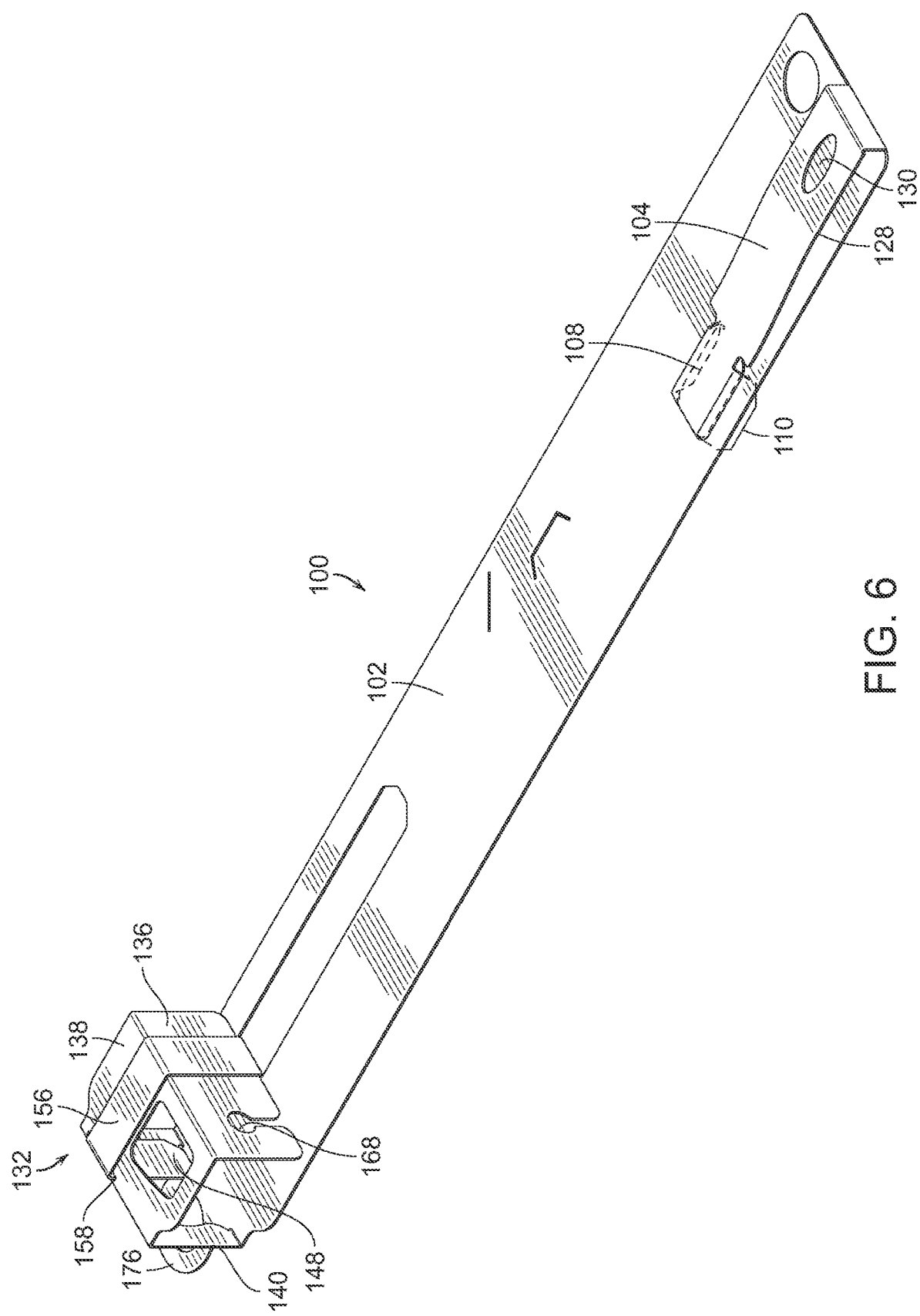
FIG. 6 is a side perspective view illustrating the backer card of FIG. 5 in a folded state.
Figure 8:
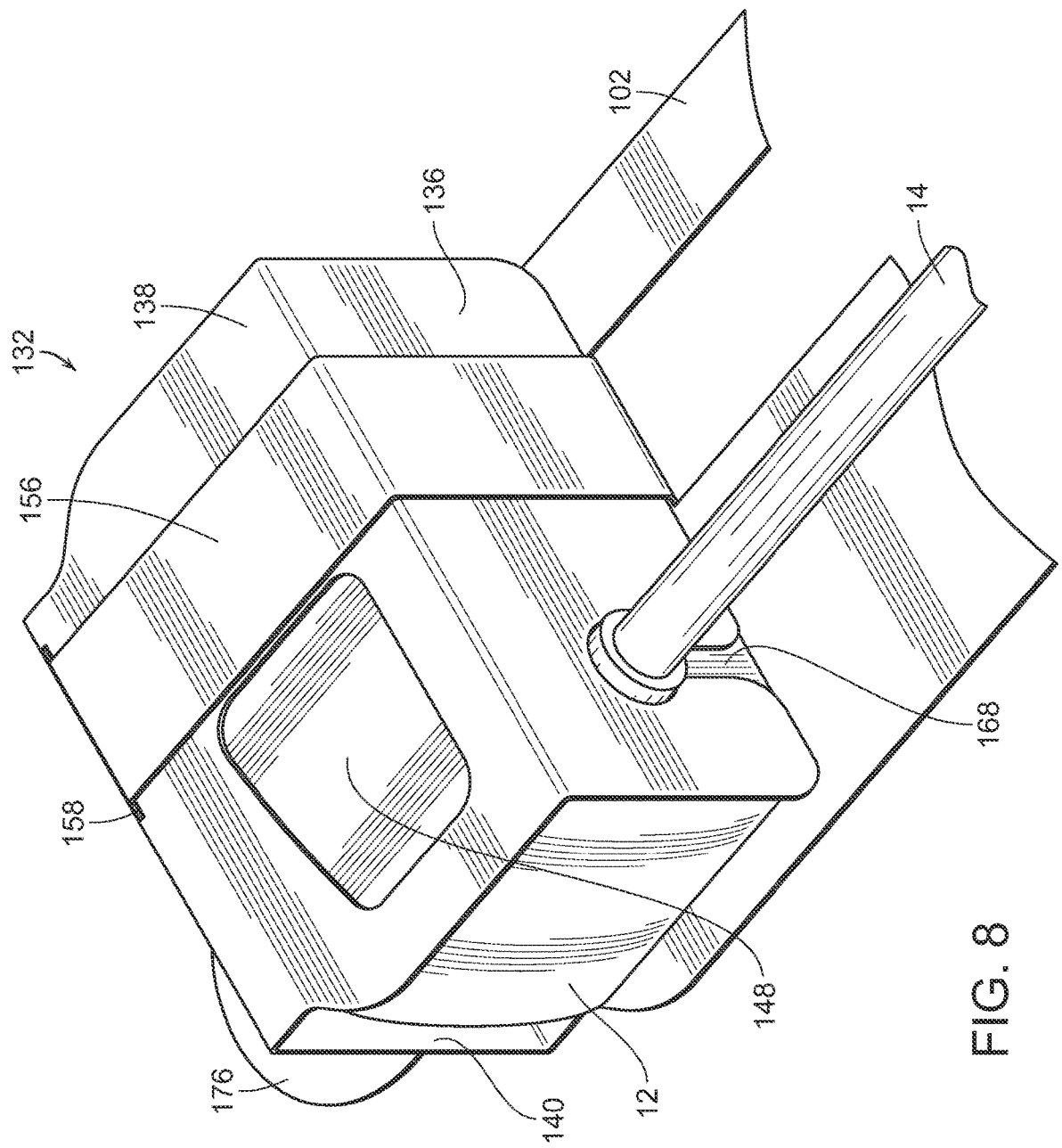
FIG. 8 is an enlarged perspective view of area "8" of FIG. 7, illustrating an end of the backer card surrounding a head of the medical instrument, in accordance with the present invention.

With reference now to FIGS. 5-7, a cutout 130 may be formed through the flap 104 so as to create a window 130 within the first flap 104. This window 130 is sized and positioned so as to reside over the end 16 of shaft 14. The window 130 may have multiple purposes. First, the window 130 enables sterilant fluid, such as steam or ETO, to more freely penetrate and pass through the pocket 128, and thus expose the end 16 of shaft 14 of the medical instrument 10 to the sterilant. The window 130 may also be used to see and visually identify the end 16 of the medical instrument 10. This may assist a user in determining the type or characteristic of the medical instrument 10.

Figure 4:
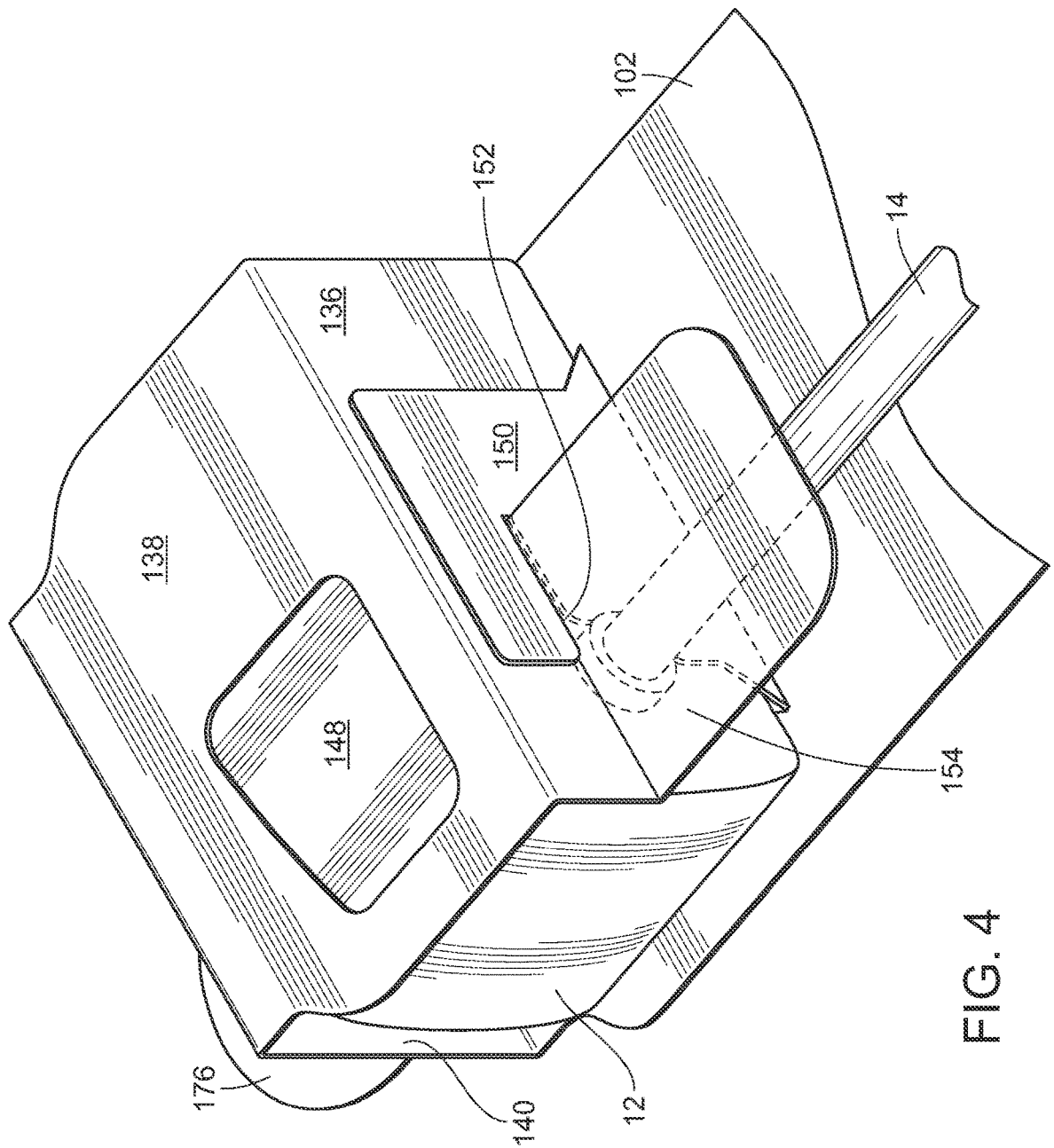
FIG. 4 is a partially fragmented and enlarged perspective view of area "4" of FIG. 3, illustrating an end of the folded backer card surrounding a head of the medical instrument, in accordance with the present invention.

With reference now to FIGS. 1-4, a second flap 132 extends away from a second end 134 of the base 102. The second flap is movable between a non-deployed position extending away from the base 102, as illustrated in FIG. 1, to a deployed position over the base 102 and forming a shell defining a compartment configured to receive the head 12 of the medical instrument therein, as illustrated in FIGS. 2-4. Typically, the second flap 132 has multiple sections foldable relative to one another to form the shell that at least partially surrounds the head 12 of the medical instrument 10. More particularly, the second flap 132 has a first section 136 defining a front wall of the shell, a second section 138 defining a top wall of the shell, and a third section 140 which defines a back wall of the shell. To facilitate manual bending and folding of the second flap between its non-deployed position extending outwardly from the base 102 to its deployed position folded over the base 102, a fold or score line 142 may be formed between the flap 132 and the base 102. Another score or fold line 144 may be formed between the top wall section 138 and the back wall section 140. Another fold or score line 146 may be formed between front wall section 136 and top wall section 138 of the second flap 132. The second flap 132 is folded at these lines so as to create the cell structure which at least partially surrounds the head 12 of the medical instrument 10, as illustrated in FIGS. 2 and 3. The shell is comprised of the sections 136-140 that wrap around the head 12 of the medical instrument 10 and cooperatively form with the base 102 a compartment that holds the head 12 of the medical instrument 10 therein.

A cutout 148 may be formed in the second flap 132, such as in the top wall section 138. This cutout 138 forms a window which can have multiple purposes. Similar to window 130 formed in the first flap 104, this window 148 formed in the second flap 132 can facilitate the entry and exit and flow of the sterilant medium, which may be steam or ETO. Also, the window 148 allows for easy viewing and visual identification of the head 12 of the medical instrument 10, which can provide information to the user as to the exact type of medical instrument which is being supported by the backer card 100. While window 148 can be of various configurations and sizes in the top wall section 138, preferably, the window 148 is of a configuration, size and placement, such as illustrated, wherein it occupies only a portion of the top wall 138 and is sufficiently spaced from the edges of the top wall 138 to reduce the chance of buckling of the card material during folding of the second flap 132.

A locking mechanism retains the second flap 132 into a folded, deployed position over the base 102. The locking mechanism comprises a first locking member detachable from the base and a second locking member formed in the second flap that lockingly engages the first locking member. The locking mechanism, and the first and second locking members, may take a variety of forms.

With reference to FIGS. 1-4, the first locking member comprises a wall 150 having a slot 152 formed therein. The wall 150 is generally co-planar with the base 102 until the backer card is assembled, wherein the wall 150 is partially detached from the base 102 and lifted upwardly. In this position, the front wall 136 of flap 132 and the first locking member wall 150 are disposed adjacent to one another. A wing 154 of section 136 of the flap 132 is bent outward and insertable into the slot 152 of the wall 150, as illustrated in FIGS. 2 and 4, so as to lock the folded shell structure of the deployed second flap 132 to the base 102.

With reference now to FIGS. 5-8, in this embodiment, the first locking member of the locking mechanism comprises a belt 156. The belt 156 is attached to the base 102 and generally co-planar therewith. However, the belt 156, which comprises an elongated strip, as illustrated, is partially detachable from the base 102 and raised upwardly and folded over at least a portion of the constructed and deployed flap 132, such as over front wall 136 and top wall 138 so as to be inserted into slit 158 such that the belt 156 and the deployed strap 132 are locked into place relative to the base 102. Score lines 160 and 162 may be formed in the belt 156 so as to facilitate the bending and folding of the belt 156 over walls 136 and 138 of the deployed second flap 132. The slit 158 is formed within the second flap 132, such as illustrated between the top wall section 138 and back wall section 140.

The backer card 100 may include means for holding the shaft 14 of the medical instrument 10, such that the shaft 14 will remain elevated and spaced apart from the base 102. Such may include an eyelet flap 164 which is partially detachable from the base 102 and pivotable upwardly from the base 102, as illustrated in FIG. 2. The eyelet flap 164 may include an aperture 166 or notch therethrough that receives the shaft 14 of the medical instrument 10 therein, as illustrated in FIG. 3.

With reference now to FIGS. 5-8, alternatively, or additionally, a notch 168 may be formed in the second flap 132, such as in front wall section 136 that receives the shaft 14 of the medical instrument 10 therein. The notch 168 is open-ended and may be configured so as to have a narrower width or opening at an open end thereof leading to a larger opening, such that the shaft 14 is received in snap-fit relation to the notch 168 and so that the shaft 14 will remain in place within the notch 168.

It is known in the industry to utilize sterilization indicators or integrators to confirm and visually indicate that sterilization has been complete and that the medical instrument 10 has been properly sterilized. Such may include autoclave tape or an indicator, in the form of an integrator card 20 which are designed to react to various variables of sterilization, including time, temperature, and/or steam. Temperature or steam sensitive chemicals may be layered between paper and aluminum foil or other materials on the card which melt or otherwise react during the sterilization cycle. Thus the user can quickly and easily determine if proper sterilization of the medical instrument 10 has taken place. The present invention may include a sterilization indicator card retainer formed in the base 102. Such may be comprised of slits 170 and 172 forming small flaps and/or areas for the card to be inserted into and held onto the backer card 102 during the sterilization process. Corners or edges of the sterilization indicator or integrator card 20 may be inserted into the one or more flaps 170, slits 172 or the like to hold it into place on the backer card 102.

In a particularly preferred embodiment, the backer card 100 also includes a finger hold through which a user may insert one or more fingers to move or carry the backer card 100 in a safe and sterile manner. Such may include an aperture 174 formed in the base 102, such as at one end thereof, through which the user may insert one or more fingers to hold and grasp the sterilization card 100 and the attached medical instrument 10. Alternatively, or additionally, a finger hold member 176 may extend from the base 102, such as an end thereof, and have an aperture 178 formed therethrough through which one or more fingers of the user may be inserted for the purpose of holding and carrying the backer card 100. Such may be formed, as illustrated, at the end 134 of the backer card 102 and extending into the back wall section 140 of the second flap 132, and detachably connected thereto such that as the flap 132 is lifted and folded into its deployed shell shape, the finger hold 176 remains extending outwardly from the base 102, as illustrated. The finger holds may be used to carry the medical instrument 10 and backer card 100, place them within a sterilization package, such as a peel pouch or the like or for use when removing the medical instrument 10 from the backer card 100.

Although several embodiments have been described in detail for purposes of illustration, various modifications may be made without departing from the scope and spirit of the invention. Accordingly, the invention is not to be limited, except as by the appended claims.

What is claimed is:

1. A medical instrument sterilization backer card, comprising:
a generally planar base;
a first flap extending from a first end of the base, the first flap movable from a non-deployed position extending away from the base to a deployed position folded over the base and forming an open-ended pocket configured to receive an end of a shaft of a medical instrument therein;
a second flap extending from a second end of the base, the second flap movable between a non-deployed position extending away from the base to a deployed position over the base and forming a shell defining a compartment configured to receive a head of the medical instrument therein; and
locking mechanism for retaining the second flap into a folded, deployed position over the base, wherein the locking mechanism comprises a first locking member detachable from the base and a second locking member formed in the second flap that lockingly engages the first locking member, and wherein the first locking member comprises a belt partially detachable from the base and the second locking member comprises a slit formed in the second flap, wherein the bell extends over the deployed second flap and into the slit.

2. A medical instrument sterilization backer card, comprising:
a generally planar base;
a first flap extending from a first end of the base, the first flap movable from a non-deployed position extending away from the base to a deployed position folded over the base and forming an open-ended pocket configured to receive an end of a shaft of a medical instrument therein;
tabs extending from the first flap and insertable into tab slots of the base to hold the first flap in position over the base in the deployed position;
a second flap extending from a second end of the base and having multiple sections, the second flap movable between a non-deployed position extending away from the base to a deployed position with the second flap sections being folded relative to one another to position the second flap over the base and form a shell defining a compartment configured to receive a head of the medical instrument therein; and
a locking mechanism for retaining the second flap into a folded, deployed position over the base, the locking mechanism comprising a first locking member detachable from the base and a second locking member formed in the second flap that lockingly engages the first locking member, wherein the first locking member comprises a belt partially detachable from the base and the second locking member comprises a slit formed in the second flap, wherein the belt extends over the deployed second flap and into the slit.

3. The backer card of claim 2, wherein the tabs partially inserted into the tab slots maintain the first flap in a spaced relation to the base.

4. The backer card of claim 2, including a window formed in the first flap.

5. The backer card of claim 2, wherein a top section of the second flap has a window formed therein.

6. The backer card of claim 2, including a finger hold extending from the base and having an aperture sized for insertion of a finger therethrough.

7. The backer card of claim 2, including a finger hold aperture formed through the base sized for insertion of a finger therethrough.

8. The backer card of claim 2, including a sterilization indicator retainer formed in the base.

9. The backer card of claim 2, including a notch formed in the second flap that receives the shaft of the medical instrument therein.

* * * * *